US006908598B2

(12) United States Patent
Sylvester

(10) Patent No.: US 6,908,598 B2
(45) Date of Patent: Jun. 21, 2005

(54) RUBIDLUM-82 GENERATOR BASED ON SODIUM NONATITANATE SUPPORT, AND IMPROVED SEPARATION METHODS FOR THE RECOVERY OF STRONTIUM-82 FROM IRRADIATED TARGETS

(75) Inventor: Paul Sylvester, Woburn, MA (US)

(73) Assignee: Lynntech, Inc., College Station, TX (US)

( * ) Notice: Subject to any disclaimer, the term of this patent is extended or adjusted under 35 U.S.C. 154(b) by 0 days.

(21) Appl. No.: 09/922,353

(22) Filed: Aug. 2, 2001

(65) Prior Publication Data

US 2003/0035772 A1 Feb. 20, 2003

(51) Int. Cl.$^7$ .......................... C01D 17/00; C01F 11/00; C01G 23/00

(52) U.S. Cl. ............................ 423/2; 423/249; 423/598; 502/400

(58) Field of Search ........................... 423/598, 2, 249; 502/400; 252/184

(56) References Cited

U.S. PATENT DOCUMENTS

| | | | |
|---|---|---|---|
| 3,953,567 A | | 4/1976 | Grant et al. |
| 3,957,945 A | | 5/1976 | Grant et al. |
| 4,276,267 A | | 6/1981 | Bentley et al. |
| 4,406,877 A | | 9/1983 | Neirinckx et al. |
| 4,562,829 A | | 1/1986 | Bergner |
| 4,585,009 A | | 4/1986 | Barker et al. |
| 4,597,951 A | | 7/1986 | Gennaro et al. |
| 5,167,938 A | | 12/1992 | Heaton et al. |
| 5,190,735 A | | 3/1993 | Phillips et al. |
| 5,296,203 A | | 3/1994 | Phillips et al. |
| 5,330,731 A | | 7/1994 | Heaton et al. |
| 5,885,925 A | * | 3/1999 | DeFilippi et al. ........... 423/608 |
| 5,966,583 A | | 10/1999 | Taylor et al. |
| 5,989,434 A | * | 11/1999 | Lundquist et al. .......... 210/679 |
| 6,106,799 A | * | 8/2000 | Lehto et al. ................ 423/598 |

FOREIGN PATENT DOCUMENTS

| | | | |
|---|---|---|---|
| EP | 0 043 650 A | | 11/1981 |
| WO | 97/14652 | * | 4/1997 |

OTHER PUBLICATIONS

Lehto et al., "The ion exchange of strontium on sodium titanate . . . " J. Radioanal. Nucl. Chem., Letters 118, 1, 1–13, 1987, no month.*
Gopal B. Saha, Raymundo T. Go, William J. Jacintyre, Thomas H. Marwick, Annette Beachler, Janet L. King and Donald R. Neumann; "Use of the $^{82}$Sr/$^{82}$Rb Generator in Clinical PET Studies"; Nucl. Med. Biol. vol. 17, No. 8. pp. 763–768–1990, no month.
International Search Report, Application No. PCT/US 02/41676, International Filinjg Date Dec. 30, 2002, 4 sheets.

Paul Sylvester and Abraham Clearfield, Solvent Extraction and Ion Exchange, 16 (6), 1527–1539 (1998), The Removal of Strontium and Cesium From Simulated Hanford Groundwater Using Inorganic Ion Exchange Materials, no month.
Yukio Yano, Essentials of a Rudidium82 Generator for Nuclear Medicine, 1987,Appl. Radiat. Isot. vol. 38. No. 3. pp 205–211, no month.
Y. Yano, T F Budinger, J L Cahoon, and R H Huesman, An Automated Microprocessor–Controlled Rb–82 Generator for Positron Emission Tomography Studies, ©1984, pp 97–122, no month.
Furn F. Knap, Jr., Thomas A Butler, New Systems For Nuclear Medicine Applications, ACS Symposium Series 241, Radionuclide Generators, Mar. 20–25, 1983, Contents.
Elizabeth A Behrens, Paul Sylvester, Gina Graziano, and Abraham Clearfield, Science and Technology for Disp;osal of Radioactive Tank Wastes, N J Lombardo, Planum Press, New York, 1998, pp 287–299, no month.
K E Thomas and J W Barnes, Large Scale Isolation of Sr–82 for Generation Production, 1984, p 123 Radionuclide Generators, American Chemical Society, no month.
LANL Procedure MRDP–PSR82Rb–03, Isolation and Purificaiton of $^{82}$Sr from Irradiated Rb Metal Targets, Mar. 18, 1998.
LANL Procedure MRDP–PSR82–05, Isolation and Purification of $^{82}$Sr in Sulfate Media after $H_2O_2$ Dissolution of Molybdenum Targets, Rev. 8, 1997.
Elizabeth A Behrens, Paul Sylvester and Abraham Clearfield, Assessment of a Sodium Nonatitanate and Pharmacosiderite–Type Ion Exchangers for Strontium and Cesium Removal from DOE Waste Simulants, Environ Sci. Technol, 1998, 32, 101–107, no month.
Paul Sysvester, Elizabeth A Behrens, Gina M Graziano, and Abraham Clearfield, An Assessement of Inorganic Ion–Exchange Materials for the Removal of Strontium from Simulated Hanford Tank Wastes, Sepration Science and Technology, 34 (10), pp 1981–1992, ©1999, no month.
Elizabeth A Behrens, Damodara M. Poojary, and Abraham Clearfield, Syntheses, Crystal Structures, and Ion–Exchange Properties of Porous Tianosilicates, $HM_3Ti_4O_4(SiO_4)_3 4H_2O$ (M=H$^+$, K$^+$, Cs$^+$), Structural Analogues of the Mineral Pharmacosiderite, Chem. Mater. 1996,8, 1236–1244, no month.

(Continued)

*Primary Examiner*—Steven Bos
(74) *Attorney, Agent, or Firm*—Streets & Steele; Jeffrey L. Streets; Frank J. Campigotto

(57) ABSTRACT

Sodium nonatitanate compositions, a method using the composition for recovery of 82Sr from irradiated targets, and a method using the composition for generating 82Rb. The sodium nonatitanate materials of the invention are highly selective at separating strontium from solutions derived from the dissolution of irradiated target materials, thus reducing target processing times. The compositions also have a very low affinity for rubidium, making it an ideal material for use as a 82Rb generator. Sodium nonatitanate materials of this type both improve the recovery of 82Sr and provide a safer, more effective 82Rb generator system.

95 Claims, 2 Drawing Sheets

OTHER PUBLICATIONS

Figure 1:
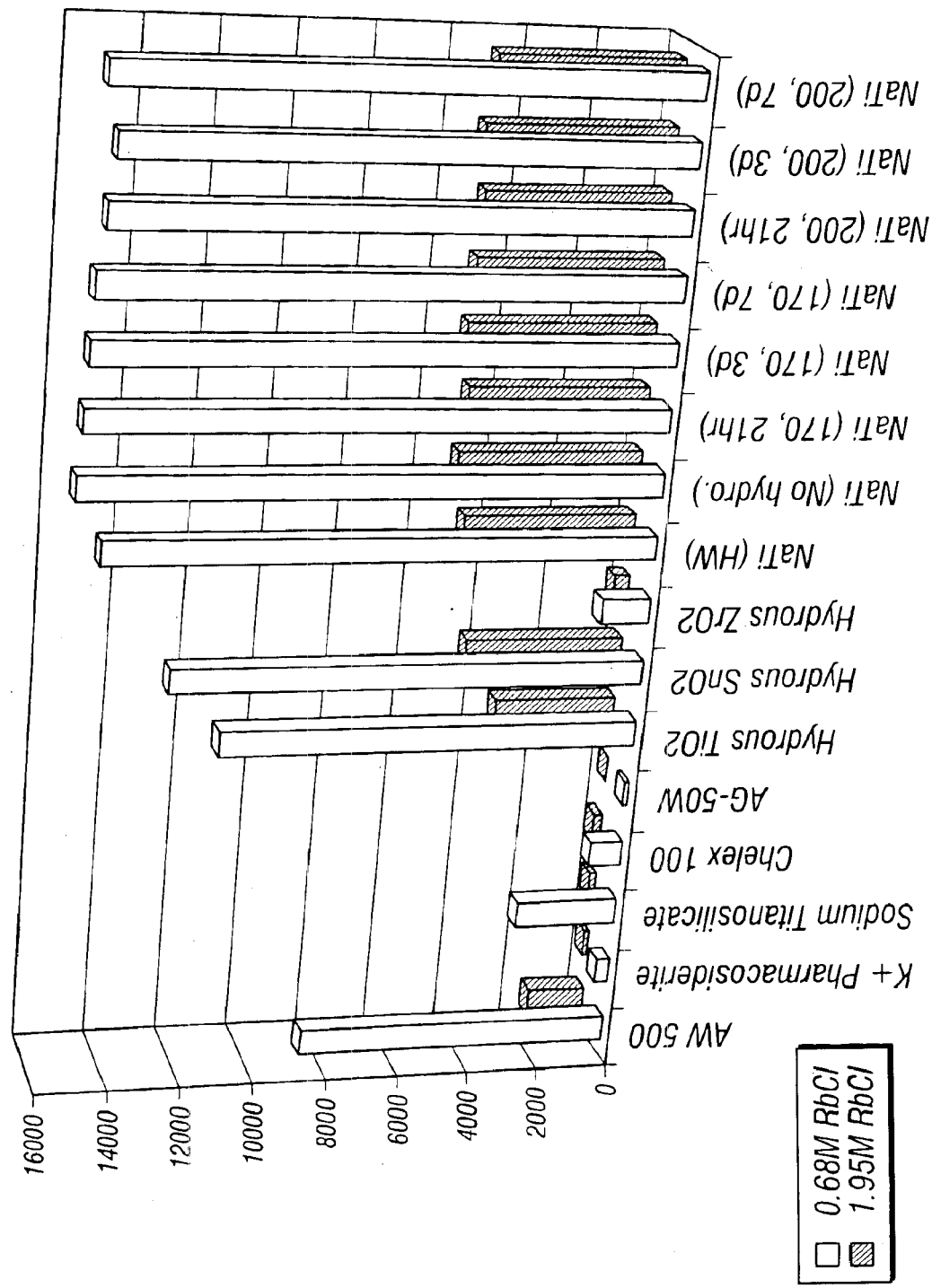

J Letho, A. Clearfield, The Ion Exchange of Strontium on Sodium Titanate $^{Na}4^{Ti}9^{O}20^{xH}2^{o}$, J Radioanal, Nucl. Chem. Letters 118/1/1 1–13 /1987, no month.

T. Jones, Pergamon Journals Ltd, Introduction: Clinical Uses of 82Sr/82Rb Generators; vol. 38 38, No. 3, pp. 171–173, 1987, no month.

International Patent WO94/19,277, Sep. 1, 1994.

A Clearfield, (ED.), :Inorganic Ion Exchange Materials, CRC Press, Boca Raton, Florida (1982), no month.

* cited by examiner

RUBIDIUM-82 GENERATOR BASED ON SODIUM NONATITANATE SUPPORT, AND IMPROVED SEPARATION METHODS FOR THE RECOVERY OF STRONTIUM-82 FROM IRRADIATED TARGETS

This invention was made with government support under grant number 1 R43 RR14986-01 awarded by the National Institutes of Health. The government has certain rights in this invention.

BACKGROUND OF THE INVENTION

1. Field of the Invention

This invention relates to the selective separation of strontium-82 from other radioisotopes, such as those resulting from an irradiated molybdenum target, and in the manufacture of a rubidium-82 generator.

2. Background of the Related Art

The use of radioisotopes as diagnostic and imaging agents in medicine has expanded rapidly in recent years. Positron ($\beta+$) emitters are particularly useful in the study of metabolic processes because the positron-electron annihilation reaction produces a pair of gamma rays with an energy level of 511 keV travelling in opposite directions. By placing a series of detectors around a patient who has been administered a positron emitter, both the location and amount of radioactivity can be accurately determined. This property is utilized in Positron Emission Tomography (PET) to image metabolic processes in vivo. Rubidium-82 (82Rb) is a short-lived positron-emitting isotope ($T_{1/2}$=75 seconds) that is increasingly being used to study blood flow through the heart and brain. Physiologically, rubidium is an analogue of potassium, and consequently enters the body's large potassium pool, which has a comparatively slow turnover. Thus, after 82Rb is injected intravenously, the tracer's uptake in tissue reflects the rate of delivery, i.e. blood flow, and thus 82Rb rapidly builds up in the heart. This can be used, for example, to study blood-brain barrier leakage and heart muscle perfusion.

The short half-life of 82Rb means that it must be supplied to physicians in the form of a generator, where the parent 82Sr ($T_{1/2}$=25 days) is immobilized on a solid substrate or support and 82Rb eluted as required. The generators that are currently available use hydrous tin oxide to immobilize the 82Sr and allow the elution of 82Rb by saline or other appropriate eluant. The 82Sr ($T_{1/2}$=25 days) is accompanied by unwanted 85Sr ($T_{1/2}$=64 days), generated as a by-product during the manufacture of 82Sr, wherein both isotopes have a relatively long half-life and a high radiotoxicity due to their tendency to accumulate in bone. Thus, it is essential to minimize or eliminate the introduction of 82Sr and 85Sr into a patient during the administration of 82Rb. Although hydrous tin oxide has proved acceptable to date for use in generators, new materials exhibiting far higher strontium affinities, improved strontium/rubidium separation factors and greater radiolytic stability are needed in order to lower the amount of 82Sr and 85Sr released during elution of the 82Rb.

The parent 82Sr is generated by the proton irradiation of rubidium, rubidium chloride or molybdenum targets followed by dissolution and processing to isolate the 82Sr. The demand for 82Rb generators has grown so great that there is a need to reduce processing times and to increase the yield of 82Sr from processed targets. One method of improving the supply of 82Sr is to improve the processes used to extract 82Sr from irradiated targets. Current methods utilize organic ion exchange or chelating resins to extract very low levels of strontium from dissolved targets containing molar concentrations of inert ions. However, a satisfactory separation of 82Sr from the target materials and other radioisotopes generated during the irradiation procedure requires multiple treatment steps due to the relatively low affinity and low selectivity of the organic ion exchange resins for 82Sr.

82Sr is produced by the proton irradiation of molybdenum metal, rubidium metal and rubidium chloride targets. The irradiation process also produces a range of other radioactive isotopes (e.g. 88Y, 88Zr, 85Sr) and as a consequence, a series of carefully designed separation procedures have been designed to separate the desired 82Sr from other radioisotopes and inactive species present. The primary method used to separate 82Sr is by a series of ion exchange and selective elution steps. Typically, AG 50 W-X8 ion exchange resin is used to separate 82Sr from dissolved targets. However, this resin is relatively non-selective and will absorb numerous polyvalent cations (e.g., 88Y) in addition to the desired 82Sr. Consequently, multiple separation steps are required to isolate 82Sr from the other isotopes present.

82Rb can be conveniently supplied to physicians in the form of a generator in which the parent 82Sr is immobilized on an ion exchange material and the 82Rb eluted when required. This means that 82Rb PET can be performed at clinical facilities where a typical generator may last several months before the yield of 82Rb diminishes below a usable level.

To be suitable for use in a 82Rb generator, an ion exchange material must exhibit a high affinity for strontium but a low affinity for rubidium, allowing the 82Rb daughter to be eluted from a column containing immobilized 82Sr. Generators have been proposed that were based on a number of separation media including CHELEX 100 ion exchange material, $Al_2O_3$, Sb(V) hexacyanoferrate, polyantimonic acid, titanium vanadate and hydrated tin(IV) oxide, with the hydrated tin(IV) oxide being the most widely used.

However, the crucial component of any system is the actual ion exchange material containing the immobilized 82Sr parent. Current systems using hydrous tin oxide have a limited life due to the breakdown of the hydrous tin dioxide, necessitating frequent replacement.

Therefore, there is a need for a highly strontium selective ion exchange material in place of ion exchange resins and hydrated tin(IV) oxide, so that the separation and recovery of 82Sr from Rb, RbCl and Mo targets is greatly facilitated. This will lead to a reduction in processing steps, a decrease in target processing times and thus a decrease in the cost of the 82Sr product. There is also a need for an ion exchange material suitable for use as a 82Rb generator having a very high selectivity for 82Sr and a very low selectivity for 82Rb to allow elution of the 82Rb by isotonic saline or other solutions.

SUMMARY OF THE INVENTION

The present invention provides a method of chemically isolating strontium-82 from proton-irradiated molybdenum targets. This comprises dissolving the molybdenum metal target containing the strontium-82, adjusting the pH of the dissolved molybdenum target solution to an alkaline pH, removing precipitates from the solution, and then absorbing the strontium-82 from the solution onto a support comprising sodium nonatitanate. Sodium nonatitanate can also be applied to the efficient recovery of strontium-82 from alkaline RbCl solutions produced during the processing of proton-irradiated rubidium metal and rubidium chloride targets.

The present invention also provides a rubidium-82 generator, comprising a strontium-82 support medium comprising sodium nonatitanate. Preferably, the sodium nonatitanate is characterized by a strontium selectivity greater than 250,000 mL/g at an alkaline pH, and/or the sodium nonatitanate is characterized by a rubidium selectivity less than 100 mL/g at an alkaline pH. More preferably, the sodium nonatitanate is characterized by a strontium/rubidium separation factor greater than 1,000, and even more preferably greater than 100,000.

The rubidium-82 generator is prepared by a process comprising: preparing sodium nonatitanate from titanium isopropoxide and aqueous sodium hydroxide; heating the sodium nonatitanate at a temperature between 100° C. and 250° C. for a period between 12 hours and 2 weeks; and absorbing strontium-82 on the sodium nonatitanate from an aqueous solution comprising strontium-82 and a soluble sodium salt, wherein the sodium salt concentration is between 0.1 and 1 molar. It is also preferred that the titanium isopropoxide and the aqueous sodium hydroxide solution are provided at a sodium hydroxide to titanium isopropoxide molar ratio of greater than 0.44, but preferably providing a large molar excess of sodium hydroxide. The sodium hydroxide to titanium isopropoxide molar ratio is preferably between 1 and 10, more preferably between 2 and 6, and most preferably about 4.

Furthermore, the invention provides a process for preparing a solution containing rubidium-82. The process comprises providing a solution containing strontium-82 at a pH between 10 and 14, absorbing the strontium-82 from the solution onto a sodium nonatitanate support medium, and eluting rubidium-82 from the sodium nonatitanate support medium with a solvent. The solvent is preferably selected from the group consisting of water and saline solutions. More particularly, the solvent may be an aqueous solution having a sodium chloride concentration between 0.001 molar and 1 molar, preferably between 0.2 molar and 1 molar. The solvent may also be a pharmaceutical grade isotonic saline and buffer solution.

DETAILED DESCRIPTION OF THE INVENTION

The present invention provides improved sodium nonatitanate compositions, a method using the composition for recovery of 82Sr from irradiated targets, and a method using the composition for generating 82Rb. The sodium nonatitanate materials of the invention are far more selective at separating strontium from solutions derived from the dissolution of irradiated target materials than current ion exchange resins used in the production of 82Sr. The present invention reduces the number of processing steps required, and thus leads to a decrease in target processing times and a reduction in the cost of the 82Sr product. Waste generation and disposal are also decreased.

According to the present invention, synthetic conditions are adjusted to produce a material with improved properties more applicable to 82Sr processing. The sodium nonatitanate of the present invention has been found to have a very low affinity for rubidium in addition to an exceptionally high affinity for strontium, making it ideal for use as a replacement for the hydrous tin dioxide used in current 82Rb generators. Sodium nonatitanate materials of this type will both improve the recovery of 82Sr and lead to a safer, more effective 82Rb generator system for clinical applications.

Sodium nonatitanate, $Na_4Ti_9O_{20} \cdot xH_2O$, is an inorganic ion exchange material that has been used for the removal of 90Sr from neutral and alkaline nuclear wastes. The sodium nonatitanate of the present invention has a number of advantages over conventional organic ion exchange resins (e.g., CHELEX 100 ion exchange material) that include: very high selectivity for trace levels of strontium in the presence of molar concentrations of other ions at alkaline pH; very low affinity for rubidium; excellent radiation, chemical and thermal stability so that there is no release of contaminants (e.g. Ti) into the 82Rb product; rapid reaction kinetics; high cation exchange capacity; absorbed ions readily stripped by treatment with dilute mineral acid allowing the sodium nonatitanate to be recycled, if desired; scale up of similar synthesis has already been demonstrated; and the sodium nonatitanate powder can be manufactured into pellets appropriate for column operations. Other chemically related sodium titanate materials suitable for use in the same manner as the aforementioned sodium nonatitanate ($Na_4Ti_9O_{20} \cdot xH_2O$) include other titanate materials exhibiting high Sr affinity and low Rb affinity, including Sr-Treat (available from Selion Oy) and monosodium titanate (available from Boulder Scientific). It is also anticipated that analogous zirconates may exhibit similar properties.

The invention also provides important improvements in the processing of irradiated targets to recover 82Sr. Sodium nonatitanate has a much greater affinity for 82Sr than currently used ion exchange resins, and a low affinity for other radioactive isotopes. Consequently, the use of sodium nonatitanate greatly simplifies the extraction process by reducing the number of separation steps that are required to produce chemically pure 82Sr. Thus, targets can be processed more rapidly and the recovery of 82Sr improved. Improved isotope selectivity may also facilitate the isolation of other useful isotopes from the targets, leading to greater payback from target processing operations.

Furthermore, less than 1 g of sodium nonatitanate material is needed in a 82Rb generator and 1 kg of this material is expected to be sufficient to process a large number of targets, even if the sodium nonatitanate material is not recycled and is disposed of after one use. Consequently, the additional cost incurred by the use of sodium nonatitanate will be negligible in comparison with the cost savings achieved in the 82Sr production.

It has been determined that replacing hydrous tin dioxide with sodium nonatitanate reduces the amount of 82Sr released during the operation of the 82Rb generator, thereby reducing the exposure of the patient to 82Sr. Sodium nonatitanate is also more chemically stable and less likely to leach non-radioactive contaminants into solution during operation of the generator. The sodium nonatitanate is also more amenable to recycling since the 82Sr can readily be stripped with mineral acid without producing additional impurities. Recycling of 82Sr generators is already being used as a source of additional 82Sr, and improvements to the recycling procedure (obtained by using a superior ion exchange material) will facilitate the recovery of 82Sr from this source.

Although the sodium nonatitanate may be used as a direct replacement for hydrous tin dioxide in the 82Rb generator, it is also possible to use sodium nonatitanate in the form of a disposable add-on filter that could be used to trap any 82Sr that is leached from the generator during the production of 82Rb.

The first step in preparing a 82Rb generator is to load the parent 82Sr onto the sodium nonatitanate material and place the ion exchange material into a suitable column. It is essential that sufficient time be allowed for the 82Sr to be absorbed by the sodium nonatitanate material in order to maximize the loading of the parent radioisotope per gram of ion exchange material.

Sodium nonatitanate should be loaded with 82Sr before being placed in an ion exchange column, to avoid preferential loading of the 82Sr on the top of the ion exchange column rather than uniformly throughout the material. This high concentration of radioactivity on a very small volume may result in undesirable radiolytic problems. Although sodium nonatitanate has been shown to be highly resistant to radiation damage, it is considered prudent to avoid any potential problems.

EXAMPLES

These Examples investigated the suitability of sodium nonatitanate for the use in separating 82Sr from irradiated targets and in the construction of a 82Sr/82Rb generator. Initial batch experiments compared the rubidium and strontium selectivities of a number of different sodium nonatitanate samples with commercially available ion exchange materials (e.g. AW 500 ion exchange material, CHELEX 100 ion exchange material) and some experimental materials that had also exhibited high strontium selectivities (e.g. sodium titanosilicate). Column experiments were then performed using target simulants and generator simulants on materials that exhibited favorable selectivity characteristics. Some work was also performed to investigate the likely interference from other isotopes present in irradiated targets on the production of 82Sr.

Example 1

Preparation of Sodium Nonatitanate

Sodium nonatitanate (NaTi) was synthesized hydrothermally as follows. 77.5 g of titanium isopropoxide was added to 84.35 g of a 50 wt. % solution of NaOH with vigorous stirring and 60 mL of deionized water was added. The resultant gel was heated at approximately 108° C. for 3 hours, transferred to a hydrothermal pressure vessel with an additional 90 mL of deionized water, and heated at either 170° C. or 200° C. for times ranging from 21 hours to 1 week. After the allotted time, the materials were filtered, washed with ethanol to remove residual base and dried at 60° C. The mass of sodium nonatitanate produced was approximately 31 g. Each sample was characterized using x-ray powder diffraction (XRD). The reaction is outlined in Equation 1.

$$9Ti(OC_3H_7)_4 + 4NaOH(aq) \rightarrow Na_4Ti_9O_{20} \cdot xH_2O + 9C_3H_7OH \quad (1)$$

The crystallinity of the material was shown to be dependent upon the reaction time and temperature, with the most crystalline materials being produced after 1 week of hydrothermal treatment (200° C. for 7 days). Samples that received no hydrothermal treatment, or only a few days, were virtually amorphous with only a few very broad reflections visible on the XRD pattern.

The theoretical cation exchange capacity (CEC) of sodium nonatitanate is quite high and has a value of 4.74 meq/g, which compares favorably with organic ion exchange resins.

Alternative titanium salts that could be used to manufacture sodium nonatitanate include titanium tetrachloride, $TiCl_4$, and titanium sulfate, $TiOSO_4 \cdot xH_2SO_4 \cdot yH_2O$. However, hydrolysis of these salts leads to the generation of hydrochloric acid and sulfuric acid, respectively, and thus additional base is required during the hydrothermal process. The final product also needed to be exhaustively washed to remove residual sodium chloride or sodium sulfate. Consequently, titanium isopropoxide (which hydrolyzes to form propanol) is the preferred starting material because the final product is free from additional sodium salts.

Example 2

Determination of Strontium Selectivity

Sodium nonatitanate and a variety of other ion exchange materials were obtained and evaluated for use in the separation of 82Sr from targets and in a 82Rb generator. These materials are described below in Table 1.

TABLE 1

Characteristics of ion exchange materials evaluated in this study.

| Material | Source | Sample Preparation |
|---|---|---|
| Na-Clinoptilolite | GSA Resources, AZ | Ground to powder. |
| AW500 | Aldrich (1.6 mm Pellets) | Ground to powder. |
| Hydrous $SnO_2$ | Synthesized in house | NaOH + $SnCl_4$. Washed with acetic acid/sodium acetate buffer. |
| K+ Pharmacosiderite ($K_3H(TiO)_4(SiO_4)_3 \cdot 4H_2O$) | Synthesized according to literature method. | None. Used as synthesized. |
| Sodium Titanosilicate ($Na_2Ti_2O_3SiO_4 \cdot 2H_2O$) | Synthesized according to literature method. | None. Used as synthesized. |
| AG 50W-X8 (Na+) ion exchange material (25–50 Mesh) | BioRad. Strong acid ion exchange resin. | Converted to Na+ form (for alkaline solutions only) |
| CHELEX 100 ion exchange Material (Na+) (50–100 Mesh) | BioRad. Chelating resin with iminodiacetic acid functionality. | None. Used as received. |
| Sodium Nonatitanate | Honeywell, IL | None. Used as received. |
| Hydrous $SiO_2$ | Synthesized in house | Acetic acid hydrolysis of tetraethyl orthosilicate. Washed with $H_2O$ |
| Hydrous $TiO_2$ | Synthesized in house | Hydrolysis of titanium isopropoxide. Washed with $H_2O$ |
| Hydrous $ZrO_2$ | Synthesized in house | $ZrOCl_2$ + NaOH. Washed with deionized water. |

The strontium selectivity of the ion exchange materials of Table 1 was evaluated in sodium chloride and rubidium chloride solutions using radiotracer techniques. Samples were evaluated using a simple batch technique to allow the rapid screening of a large number of materials over a range of ionic strengths. Blanks were run for each matrix to check for any loss of strontium during filtration or absorption of strontium onto the scintillation vials. In all solutions evaluated, strontium absorption was negligible.

0.05 g of each of the ion exchange materials was contacted with 10 mL of a solution, spiked with 89Sr, in a capped scintillation vial. (The total strontium content was approximately 1.6 ppm, thus preventing any loss of strontium in solution due to precipitation of sparingly soluble $Sr(OH)_2$ at alkaline pH values.) The mixtures were shaken for 6 hours, filtered through a 0.2 $\mu$m syringe filter and the residual activity determined using liquid scintillation counting (LSC). Distribution Coefficients ($K_d$ values) were then determined according to Equation 2:

$$K_d = (A_i - A_f)/A_f * v/m \quad (2)$$

where: $A_i$=initial activity in solution (counts per minute (cpm)/mL)

$A_f$=final activity in solution (cpm/mL)

v=volume of solution (mL)

m=mass of exchanger (g)

The final pH of the solution was also noted. The period of 6 hours was chosen to allow equilibrium to be reached for each of the ion exchange materials. However, previous work on the titanosilicates and titanates had shown the reaction rates to be rapid with the majority of the uptake occurring in only a few minutes. The concentration of the chloride solutions was varied from 1M to 0.001M to evaluate the effect of increasing Rb+ and Na+ concentrations on the uptake of $Sr^{2+}$. All experiments were performed in duplicate, and if significant variations between duplicate samples occurred, the experiments were repeated until good agreements on the $K_d$ values were obtained. The results are shown in Tables 2 and 3 and represented the average $K_d$ obtained, quoted to 3 significant figures.

TABLE 2

Strontium selectivity data from unbuffered sodium chloride solutions.

| Ion Exchange Material | $K_d$ mL/g 1M NaCl | 0.1M NaCl | 0.01M NaCl | 0.001M NaCl |
|---|---|---|---|---|
| Na-Clinoptilolite | 8 | 124 | 3,260 | 36,900 |
| AW500 | 1,860 | 88,300 | 1,270,000 | 1,210,000 |
| Hydrous $SnO_2$ | 767 | 43,000 | 124,000 | 51,800 |
| K+ Pharmacosiderite | 18,300 | 251,000 | 594,000 | 281,000 |
| Sodium Titanosilicate | 556,000 | 273,000 | 119,000 | 42,900 |
| AG 50W (Na+) | 32 | 3,380 | 365,000 | 2,510,000 |
| CHELEX 100 ion exchange material (Na+) | 610 | 26,400 | 726,000 | 1,300,000 |
| NaTi (Honeywell) | 80,600 | 1,030,000 | 258,000 | 166,000 |
| NaTi (No hydrothermal) | 1,530,000 | 2,570,000 | 739,000 | 372,000 |
| NaTi (170° C., 21 hr) | 1,030,000 | 1,240,000 | 272,000 | 172,000 |
| NaTi (170° C., 3 d) | 959,000 | 633,000 | 218,000 | 93,100 |
| NaTi (170° C., 7 d) | 167,000 | 834,000 | 264,000 | 90,400 |
| NaTi (200° C., 21 hr) | 439,000 | 1,390,000 | 197,000 | 120,000 |
| NaTi (200° C., 3 d) | 261,000 | 898,000 | 251,000 | 158,000 |
| NaTi (200° C., 7 d) | 195,000 | 955,000 | 265,000 | 214,000 |
| $ZrO_2$ | 3,360 | 52,200 | 213,000 | 232,000 |

TABLE 3

Strontium selectivity data from unbuffered rubidium chloride solutions

| Material | $K_d$ mL/g 1M RbCl | 0.1M RbCl | 0.01M RbCl | 0.001M RbCl |
|---|---|---|---|---|
| Na-Clinoptilolite | 19 | 3 | 88 | 11,000 |
| AW500 | 9,750 | 107,000 | 1,020,000 | 1,280,000 |
| Hydrous $SnO_2$ | 766 | 66,100 | 104,000 | 51,800 |
| K+ Pharmacosiderite | 1,950 | 40,800 | 419,000 | 427,000 |
| Sodium Titanosilicate | 12,600 | 94,700 | 164,000 | 179,000 |
| AG-50W (Na+) | 44 | 3,870 | 237,000 | 800,000 |
| CHELEX 100 ion exchange material (Na+) | 1,580 | 38,400 | 555,000 | 977,000 |
| NaTi (Honeywell) | 13,900 | 108,000 | 279,000 | 324,000 |
| NaTi (No hydrothermal) | 14,220 | 116,000 | 345,000 | 429,000 |
| NaTi (170° C., 21 hr) | 10,500 | 71,700 | 193,000 | 205,000 |
| NaTi (170° C., 3 d) | 15,100 | 39,500 | 68,000 | 95,200 |
| NaTi (170° C., 7 d) | 23,000 | 55,800 | 31,200 | 110,000 |
| NaTi (200° C., 21 hr) | 11,000 | 66,400 | 110,000 | 103,000 |
| NaTi (200° C., 3 d) | 10,600 | 56,800 | 146,000 | 158,000 |
| NaTi (200° C., 7 d) | 10,500 | 57,400 | 146,000 | 158,000 |
| $ZrO_2$ | 3,000 | 42,400 | 184,000 | 221,000 |

Comparing the selectivity data from sodium and rubidium solutions, it is evident that rubidium ions cause a reduction in affinity for the strontium ion for all of the exchangers indicating that the affinity of these materials for rubidium is significantly higher than the affinity for sodium ions. The pH of the final solutions was generally alkaline for the nonatitanates (NaTi) and titanosilicates, with pH values as high as 12 being measured. This was due to hydrolysis of the exchangers resulting in the absorption of protons and the release of sodium ions, thus increasing the pH of the aqueous phase. This effect can be overcome, if desired, by buffering the solution.

The most distinct trend was observed in 1M NaCl solutions for the sodium nonatitanate samples. The highest $K_d$ was observed for the non-hydrothermal material and the $K_d$ values decreased with increasing reaction time for both the 200° C. and 170° C. materials. Clearly, strontium uptake is facilitated by having a low-crystallinity material. This suggests that as the crystallinity increases and the size of the nonatitanate crystallites also increases, it becomes thermodynamically less favorable for exchange of the sodium ions by strontium. It is also interesting to note that the majority of the sodium nonatitanates exhibit a higher selectivity for strontium in 1M NaCl than in 0.001M NaCl. This indicates that the higher ionic strength facilitates the $Na^+/Sr^{2+}$ exchange reaction and more than compensates for the increased competition for the ion exchange sites from the additional Na+ ions.

This data shows that sodium nonatitanate is an ideal material for the recovery of 82-Sr from irradiated rubidium and rubidium chloride targets and in the manufacture of a 82-Rb generator.

Example 3

Rubidium Selectivity from NaCl Solutions

For an ion exchange material to be suitable for use in a 82Rb generator, it must have a very high selectivity for strontium to prevent any loss of 82Sr from the ion exchange column and release to the patient undergoing a PET scan. This property was clearly demonstrated in Example 2. It must also have a very low selectivity towards rubidium, thus allowing 82Rb to be released into solution as saline is passed through the 82Rb generator. Consequently, the rubidium selectivity of the ion exchange materials was evaluated in sodium chloride media following the procedure described in Example 2. The same procedure was followed using 86Rb to spike the solutions to give an activity of approximately 200,000 cpm/mL. Total rubidium in solution was <0.05 ppm. The selectivities of the materials are shown below in Table 4.

TABLE 4

Rubidium selectivity data from unbuffered sodium chloride solutions.

| Material | 86 Rb $K_d$ mL/g 1M NaCl | 0.1M NaCl | 0.01M NaCl | 0.001M NaCl |
|---|---|---|---|---|
| AW500 | 116 | 620 | 4,920 | 21,900 |
| Hydrous $SnO_2$ | 1 | 6 | 36 | 290 |
| K+ Pharmacosiderite | 148 | 475 | 2,030 | 4,020 |
| Sodium Titanosilicate | 8,010 | 194,000 | 114,000 | 75,800 |
| AG 50W (Na+) | 7 | 75 | 688 | 6,680 |
| CHELEX 100 ion exchange material (Na+) | 3 | 8 | 43 | 256 |
| NaTi (Honeywell) | 9 | 102 | 488 | 817 |
| NaTi (No hydrothermal) | 4 | 59 | 280 | 446 |
| NaTi (170° C., 21 hr) | 9 | 56 | 209 | 297 |
| NaTi (170° C., 3 d) | 7 | 46 | 198 | 311 |
| NaTi (170° C., 7 d) | 3 | 15 | 47 | 71 |
| NaTi (200° C., 21 hr) | 8 | 79 | 334 | 502 |
| NaTi (200° C., 3 d) | 8 | 52 | 207 | 307 |
| NaTi (200° C., 7 d) | 4 | 25 | 111 | 178 |
| $ZrO_2$ | 1 | 12 | 60 | 154 |

TABLE 4A

Strontium-Rubidium Separation Factor

| Ion Exchange Material | 1M NaCl | 0.1M NaCl | 0.01M NaCl | 0.001M NaCl |
|---|---|---|---|---|
| AW500 | 16.0 | 142 | 258 | 55.3 |
| Hydrous SnO2 | 767 | 7,167 | 3,444 | 179 |
| K+ Pharmacosiderite | 124 | 528 | 293 | 69.9 |
| Sodium Titanosilicate | 69.4 | 1.41 | 1.04 | 0.57 |
| AG 50W (Na+) | 4.57 | 45.1 | 531 | 376 |
| Chelex 100 (Na+) | 203 | 3,300 | 16,884 | 5,078 |
| NaTi (Honeywell) | 8,956 | 10,098 | 529 | 203 |
| NaTi (No hydrothermal) | 382,500 | 43,559 | 2,639 | 894 |
| NaTi (170° C., 21 hr) | 114,444 | 22,143 | 1,301 | 579 |
| NaTi (170° C., 3 d) | 137,000 | 1,370 | 1,101 | 299 |
| NaTi (170° C., 7 d) | 55,667 | 55,600 | 5,617 | 1,273 |
| NaTi (200° C., 21 hr) | 54,875 | 17,595 | 590 | 239 |
| NaTi (200° C., 3 d) | 32,625 | 17,269 | 1,213 | 515 |
| NaTi (200° C., 7 d) | 48,750 | 38,200 | 2,387 | 1,202 |
| ZrO2 | 3,360 | 4,350 | 3,550 | 1,506 |

TABLE 4B

Percent Rubidium Retention Generated on 0.1 g of Exchanger after Elution with 50 mL of NaCl Solution, mCi per 100 mCi

| Ion Exchange Material | 1M NaCl | 0.1M NaCl | 0.01M NaCl | 0.001M NaCl |
|---|---|---|---|---|
| AW500 | 18.8 | 55.4 | 90.8 | 97.8 |
| Hydrous Sn2 | 0.2 | 1.2 | 6.7 | 36.7 |
| K+ Pharmacosiderite | 22.8 | 48.7 | 80.2 | 88.9 |
| Sodium Titanosilicate | 94.1 | 99.7 | 99.6 | 99.3 |
| AG 50W (Na+) | 1.4 | 13.0 | 57.9 | 93.0 |
| Chelex 100 (Na+) | 0.6 | 1.6 | 7.9 | 33.9 |
| NaTi (Honeywell) | 1.8 | 16.9 | 49.4 | 62.0 |
| NaTi (No hydrothermal) | 0.8 | 10.6 | 35.9 | 47.1 |
| NaTi (170° C., 21 hr) | 1.8 | 10.1 | 29.5 | 37.3 |
| NaTi (170° C., 3 d) | 1.4 | 8.4 | 28.4 | 38.3 |
| NaTi (170° C., 7 d) | 0.6 | 2.9 | 8.6 | 12.4 |
| NaTi (200° C., 21 hr) | 1.6 | 13.6 | 40.0 | 50.1 |
| NaTi (200° C., 3 d) | 1.6 | 9.4 | 29.3 | 38.0 |
| NaTi (200° C., 7 d) | 0.8 | 4.8 | 18.2 | 26.3 |
| ZrO2 | 0.2 | 2.3 | 10.7 | 23.5 |

From the data in Table 4, it is clear that the all of the sodium nonatitanate materials have a very low affinity for rubidium, particularly in the presence of relatively high amounts of sodium ions. In general, the rubidium selectivity decreased with increasing reaction time for both series of nonatitanates (170° C. and 200° C.) with the lowest affinity being demonstrated by the sample that was heated hydrothermally at 170° C. for 1 week. Uptake was negligible in 1M NaCl and the very low reduction in activity that was noted could be accounted for by absorption of rubidium during filtration and by pipetting errors during the counting procedure. Consequently, samples with $K_d$ values that were below 10 mL/g can be considered to have no affinity at all for 86Rb. Some rubidium uptake was evident in very dilute sodium solutions, but the $K_d$ values were low for all of the titanate samples. This suggests that the uptake of rubidium was more likely due to the materials having an exceptionally low affinity for sodium rather than any real affinity for rubidium. All of the sodium nonatitanate materials performed better than the commercially available sample obtained from Honeywell Inc. The materials are clearly ideal for use in a 82-Rb generator.

Hydrous tin dioxide exhibited some of the lowest rubidium affinities and was comparable with CHELEX 100 ion exchange material, the best of the nonatitanates and the hydrous zirconium dioxide. However, hydrous tin dioxide exhibited much lower strontium $K_d$ values than the nonatitanates. Therefore, nonatitanate materials are preferred because they have higher strontium/rubidium separation factors. Hydrous tin dioxide also has a limited pH stability range and significant dissolution and release of absorbed strontium is likely to occur should any significant pH perturbations occur outside the range of pH 4 to pH 9. Radiation stability of hydrous tin dioxide is also limited, with particle breakdown causing current 82-Rb generators to be replaced before decay has reduced the 82-Rb below useable levels.

The rubidium selectivity data also indicates that AW500, potassium Pharmacosiderite and the sodium titanosilicate have a strong affinity for rubidium in a range of saline solutions. Consequently, these materials will be unsuitable for use in a 82Rb generator and have only limited applications in the processing of irradiated target materials.

Example 4

Sr and Rb Selectivity in 0.1M Sodium Acetate/Acetic Acid Buffer

In order to prevent hydrolysis reactions from raising the pH as described above, some strontium and rubidium selectivity experiments were performed in a 0.1M sodium acetate/acetic acid buffer solution. In these tests, the final pH remained between 5.2 and 6.3, which is a more clinically acceptable pH for an 82Rb infusion. Rubidium $K_d$ values remained low, as expected, following the trend observed in Table 5. Strontium $K_d$ values were considerably lower, with a maximum $K_d$ value of 80,000 mL/g being obtained for the sodium nonatitanate sample that was heated hydrothermally at 170° C. for 21 hours. This is considerably lower than the $K_d$ value of over 1,200,00 mL/g that was obtained in unbuffered 0.1M NaCl. The $K_d$ values obtained for the other ion exchange materials were also considerably lower. However, the Sr/Rb separation factors remained high and the sodium nonatitanates still outperformed hydrous tin dioxide and the organic ion exchange resins. The affinity of sodium nonatitanate for strontium is greatest at higher pH values.

Example 5

Molybdenum Targets

The basic steps of a proposed process to obtain 82Sr from irradiated molybdenum targets are as follows:
1. Dissolve the irradiated molybdenum target in 30% hydrogen peroxide, ensuring excess hydrogen peroxide is destroyed.
2. Add sodium hydroxide to bring the pH to approximately 12.
3. Filter the solution to remove any precipitate. It is predicted that the majority of 88Zr and 59Fe will be found in the precipitate, and experiments already performed have confirmed that 99% or more of the 88Y precipitated out of solution on the addition of NaOH.
4. Pass the solution through a column of sodium nonatitanate and wash the column with two bed volumes of 0.1M NaCl, adjusted to pH 12 with NaOH. 82Sr and 85Sr will be absorbed. 82Rb and other Rb isotopes will remain in the aqueous phase. Molybdate anions will also pass through the column.
5. The column can then be stripped using dilute mineral acid to recover the 82Sr and the sodium nonatitanate reused or discarded.

There is a range of other isotopes present in addition to 82Sr, including 75Se, 73As, 74As, 7Be, 68Ge, 48V, 60Co (and other Co isotopes), 54Mn, 51Cr and 95mTc. In the alkaline target solution, Se, As, V, Ge, Cr, Mn and Tc are expected to be present as anions and thus will not be absorbed onto the sodium nonatitanate. Significant amounts of Co would be expected to precipitate when the target solution is neutralized, and thus little is expected to be available under alkaline conditions to absorb onto the sodium nonatitanate. The most likely isotope to be absorbed is beryllium, because it is a Group II metal with a similar aqueous chemistry to strontium. However, the affinity of sodium nonatitanate for Group II metals decreases in the order Sr>Ca>Mg. No data is available for beryllium, but if the trend continues, the affinity would be expected to be low. Thus, any absorbed 7Be would be readily removed by an alkaline sodium chloride (or similar) wash.

The current process for recovering 82Sr from irradiated rubidium metal and rubidium chloride targets requires minimal modification to facilitate the use of sodium nonatitanate. Both targets are processed following standard processing procedures to generate rubidium chloride solutions in an ammonia/ammonium chloride buffer solution. These solutions are then passed through a sodium nonatitanate column and washed with additional buffer to remove any weakly held rubidium cations. Strontium and possibly some other cationic species present will be absorbed onto the nonatitanate column, whereas rubidium cations, ammonium cations and anions will rapidly pass through the column. If additional cations are absorbed onto the sodium nonatitanate, they can be selectively removed by washing with an appropriate eluant (e.g. citrate, nitrilotriacetate.) The strontium selectivity of sodium nonatitanate has been shown to be unaffected by a number of common complexants and as a consequence, it should be a relatively simple manner to elute any undesirable cations from the column, leaving pure 82/85Sr.

FIG. 1 clearly shows the exceptionally high affinity of the sodium nonatitanate materials in comparison with the currently utilized organic resin CHELEX 100 ion exchange material. All of the sodium nonatitanates performed equally well in the buffered rubidium target solutions indicating that the synthetic conditions are not too important when the material is being used in solutions containing high concentrations of rubidium ions. Thus, by replacing the CHELEX 100 ion exchange material with sodium nonatitanate, a more efficient 82Sr isolation can be achieved.

It has also been shown that it is possible to tailor the selectivity of the sodium nonatitanate to achieve the optimum Sr/Rb separation by manipulating the reaction conditions. The differing selectivities were most obvious in sodium solutions, with the less crystalline materials exhibiting the highest strontium distribution coefficients. However, the series of nonatitanates showed little difference in behavior when the predominant cation in solution was Rb+. The materials synthesized clearly demonstrated superior characteristics to the commercially available sample in almost all matrices evaluated. The majority of the sodium nonatitanate samples also exhibited greater strontium selectivities than hydrous tin dioxide in a range of sodium chloride solutions, from 1M to 0.001M. Rubidium selectivities were low, making the sodium nonatitanate ideal as a replacement for hydrous tin dioxide in a 82Rb generator.

Commercially, one method of 82-Sr production is via the proton spallation reaction with natural molybdenum metal targets. A simulated molybdate target solution was prepared as follows. 12.5 g of molybdenum powder was carefully dissolved in 30% $H_2O_2$ solution and made up to a total volume of 500 mL to produce a clear yellow solution of molybdic acid, $H_2MoO_4$. Solid sodium hydroxide granules totaling 10.9 g were then carefully added to neutralize the solution and bring the pH to approximately 12.3. The colorless solution was then filtered to remove any precipitate. This alkaline molybdate solution was spiked with either 86Rb or 89Sr and $K_d$ values determined as described previously. Separation factors for the strontium/rubidium selectivity were also calculated by dividing the strontium $K_d$ by the rubidium $K_d$, thus allowing the relative affinities of the ion exchange materials to be directly compared. The results are illustrated below in Table 5.

TABLE 5

Strontium and rubidium absorption from simulated molybdate target solutions

| Material | Sr $K_d$ mL/g | Rb $K_d$ mL/g | Separation Factor |
|---|---|---|---|
| AW500 | 7,070 | 194 | 36.4 |
| K+ Pharmacosiderite | 187,000 | 142 | 1320 |
| Sodium Titanosilicate | 547,000 | 6500 | 84.2 |
| CHELEX 100 ion exchange material (Na+) | 3,120 | 5 | 624 |

TABLE 5-continued

Strontium and rubidium absorption from simulated molybdate target solutions

| Material | Sr K$_d$ mL/g | Rb K$_d$ mL/g | Separation Factor |
|---|---|---|---|
| AG 50W-X8 (Na+) ion exchange material | 69 | 18 | 3.83 |
| NaTi (Honeywell) | 337,000 | 27 | 12,500 |
| NaTi (No hydrothermal) | 1,690,000 | 12 | 141,000 |
| NaTi (170° C., 21 hr) | 1,000,000 | 12 | 83,300 |
| NaTi (170° C., 3 d) | 829,000 | 14 | 59,200 |
| NaTi (170° C., 7 d) | 324,000 | 3 | 108,000 |
| NaTi (200° C., 21 hr) | 954,000 | 12 | 79,500 |
| NaTi (200° C., 3 d) | 687,000 | 11 | 62,500 |
| NaTi (200° C., 7 d) | 772,000 | 9 | 85,800 |
| ZrO$_2$ | 168,000 | 8 | 21,000 |

From this data, it is clear that the sodium nonatitanate materials are far superior to CHELEX 100 ion exchange material and AG 50W-X8 ion exchange material resins for the recovery of 82Sr from irradiated molybdenum targets. High K$_d$ values in excess of 500,000 mL/g indicate that almost 100% strontium removal was achieved by some of the nonatitanate samples, with the residual strontium in solution approaching background levels. In the alkaline conditions used in this test, the CHELEX 100 ion exchange material resin had the lowest affinity for strontium of all of the materials evaluated. The selectivity of the sodium nonatitanate for rubidium was lowest for the sodium nonatitanate material that was prepared by heating for 1 week at 170° C. to obtain a relatively crystalline product. However, strontium selectivity also decreased with increasing reaction time.

The best overall strontium/rubidium separation factor was obtained for the material that had not undergone any hydrothermal treatment. All of the materials performed better than the commercially available nonatitanate materials. Thus, it is possible to alter the selectivity of the material by controlling the reaction conditions to produce an improved sodium nonatitanate material for use in 82Sr separations. Rubidium selectivities were very low for all of the nonatitanates, indicating minimal rubidium absorption would occur in a column process and that any rubidium absorbed would be readily removed by a dilute saline wash.

The sodium titanosilicate, potassium Pharmacosiderite and AW500 exhibit selectivities for rubidium that are too high to allow their use in the selective removal of 82Sr from irradiated molybdenum targets. This high selectivity would result in some rubidium being retained on the column that would not be readily removed by a simple saline wash, thus leading to contamination of the 82Sr product with both radioactive and stable rubidium isotopes. Hydrous tin oxide was not evaluated because, due to the amphoteric nature of tin, significant dissolution would be expected at a pH in excess of 12.

Example 6

Acid Molybdate Target Solutions

Sodium nonatitanate has a relatively low affinity for strontium at pH values less than 6, and was not expected to exhibit any affinity for strontium from the acidic molybdate target solutions prior to the addition of sodium hydroxide. K$_d$ values were determined to confirm this and to compare it with the K$_d$ values for both CHELEX 100 ion exchange material and AG 50W-X8 ion exchange material under identical conditions. The data obtained is shown below in Table 6.

TABLE 6

The affinity of selected ion exchange materials for strontium in acidic molybdate target solutions

| Ion Exchange Material | Sr K$_d$ mL/g | Final pH of Solution |
|---|---|---|
| CHELEX 100 ion exchange material | 25 | 1.43 |
| AG 50W-X8 ion exchange material | 18,300 | 1.42 |
| Sodium Nonatitanate (Honeywell) | 1,260 | 1.53 |

These data clearly indicate that for the processing of acid molybdate solutions, the strong acid ion exchange resin AG 50W-X8 ion exchange material is the preferred medium. However, the Sr K$_d$ value of 18,300 mL/g in the acidic media is nearly two orders of magnitude lower than the K$_d$ value of 1,690,000 mL/g that was obtained for the best of the sodium nonatitanate materials in alkaline molybdate solutions. Consequently, it is evident that 82Sr can be recovered more effectively from alkaline solution using sodium nonatitanate than is currently achieved using AG 50W-X8 ion exchange material from acidic media.

Example 7

Rubidium and Rubidium Chloride Target Solutions

The processing of either rubidium chloride or rubidium metal targets follows a similar procedure once the target has been successfully dissolved. In essence, 82Sr needs to be selectively extracted from a solution of RbCl in a 0.1 M NH$_3$/0.1M NH$_4$Cl buffer adjusted to a pH of between 9 and 10. Batch experiments were performed in simulated buffer solutions to determine the strontium selectivity in the presence of high concentrations of rubidium ions. Only the ion exchange materials that exhibited high strontium selectivities in the initial scoping studies with NaCl solutions were evaluated. K$_d$ values were obtained as described previously. Two rubidium chloride solutions were selected which represent typical rubidium concentrations obtained during the processing of rubidium metal (1.95 M Rb+) and rubidium chloride targets (0.68 M Rb+). In both cases, CHELEX 100 ion exchange material is used in the preliminary step to remove the 82Sr from the buffered rubidium solutions. The K$_d$ values for the ion exchange materials are shown in FIG. 1.

In the buffered rubidium solutions, there is little difference between the different nonatitanates evaluated. This is in stark contrast to the sodium molybdate solutions where a large variation in the performance of the titanates was observed. The nonatitanates were clearly the most effective materials at removing strontium from the buffered solutions with strontium K$_d$ values of around 15,000 mL/g in 0.68 M Rb+ solutions and approximately 5,000 mL/g in 1.96 M Rb+ solutions. By contrast, CHELEX 100 ion exchange material resin gave K$_d$ values of less than 1,000 mL/g in both solutions. Hydrous titanium oxide and hydrous tin oxide also exhibited appreciable K$_d$ values, but they performed less efficiently than the nonatitanates in both solutions. Consequently, this data demonstrates that using sodium nonatitanate in place of CHELEX 100 ion exchange material resin will greatly increase the amount of strontium extracted from the target solutions.

The ion exchange materials were also evaluated for their rubidium selectivity from 0.1 M NH$_3$/0.1M NH$_4$Cl buffer solution. The buffer was prepared, spiked with 86Rb and the pH adjusted to approximately 9.25 with concentrated ammonia. 86Rb $K_d$ values were then determined following the method described earlier. All of the sodium nonatitanates had a $K_d$<20 mL/g. The very low rubidium selectivity in the pure buffer is almost certainly due to competition from $NH_4+$ ions for the available ion exchange sites. Consequently, absorption of rubidium during the processing of rubidium and rubidium chloride targets will be minimal, and any rubidium absorbed will be readily removed by washing with additional 0.1 M $NH_3$/0.1M $NH_4Cl$ buffer solution. Thus, a clean separation of 82Sr from these targets can be obtained using sodium nonatitanate.

The performance could also be improved by removing the buffer and increasing the pH to improve the amounts of strontium absorbed. (Buffers were initially utilized to maximize the performance of the organic ion exchange resins currently used and are not essential to the 82Sr recovery process.)

Example 9

Kinetic Experiments

In order for the sodium nonatitanate materials to find applications in the processing of irradiated target solutions, they must exhibit fast ion exchange kinetics allowing solutions to be passed through an ion exchange column at an acceptable rate. The kinetics of strontium absorption from alkaline molybdate target solutions was evaluated using a simple batch procedure. Ion exchange material, in the amount of 0.05 g, was shaken with 10 mL of molybdate solution spiked with 89Sr to give a total activity of approximately 155,000 cpm/mL. After an allotted time, the material was filtered through a 0.2 m syringe filter and the activity in the aqueous phase determined by LSC. The results are shown below in FIG. 2.

Figure 2:
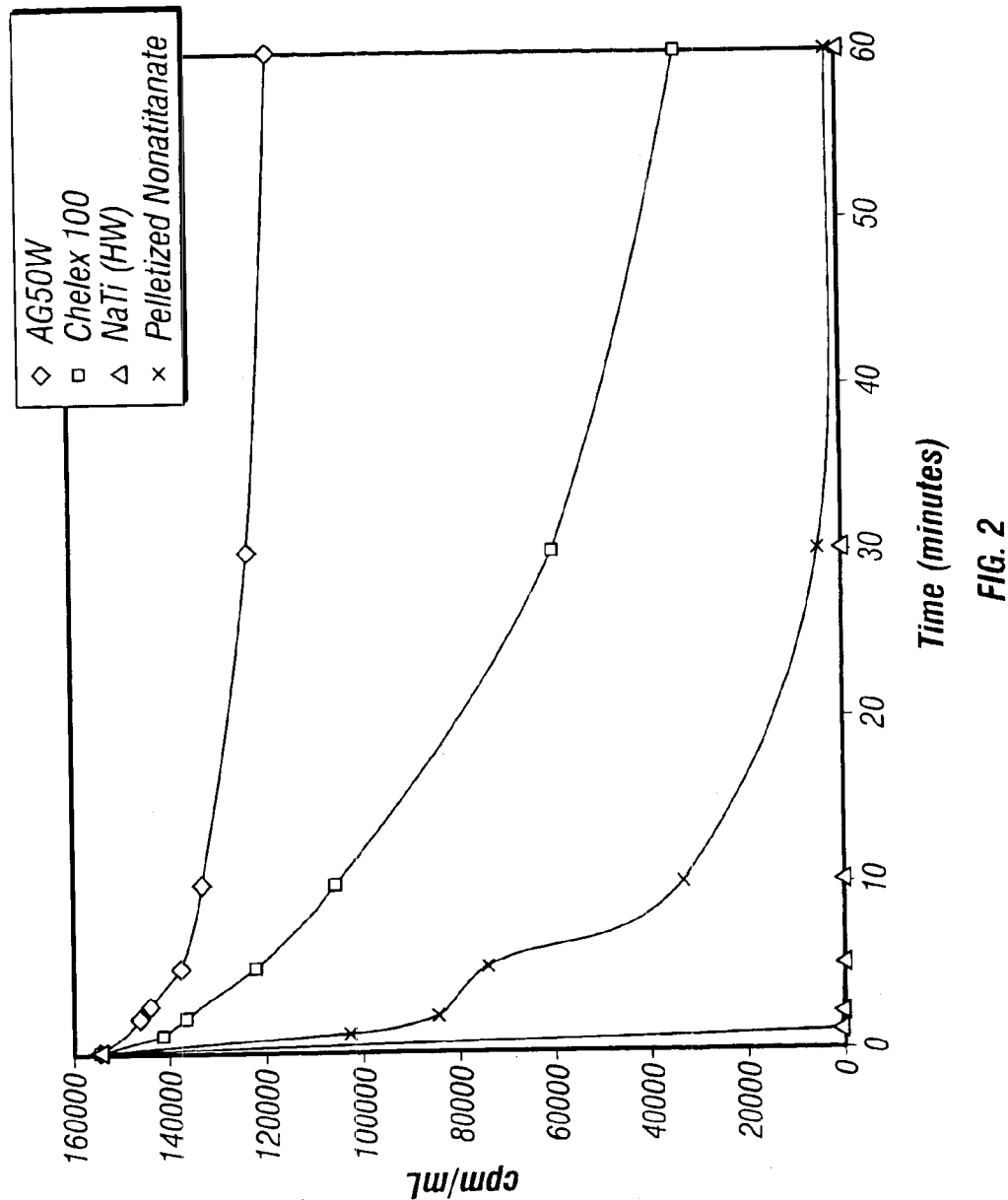

From the data in FIG. 2, it is clear that the reaction kinetics for the sodium nonatitanate powder is extremely rapid, with over 99% of the 89Sr removed in only 1 minute. By contrast, the reaction kinetics of the organic ion exchanged resins was much slower and the total amount of 89Sr removed after 1 hour was much less.

The exceedingly rapid kinetics can partly be explained by the fact that the nonatitanate was in the form of a fine powder, whereas the two resins were in the form of beads (see Table 1). As a consequence, a relatively slow reaction rate would be expected for the beads because the uptake of 82Sr will be dependent upon the rate of diffusion of the 82Sr to the internal functional groups. The rate of uptake of a sample of sodium nonatitanate pellets (using hydrous titanium dioxide as a binder) was significantly slower than the powdered form, but the kinetics and amount of 82Sr absorbed was still significantly better than for either of the two organic resins. As the pelletization process is improved, it is expected that the kinetics and selectivity of the pelletized sodium nonatitanate will improve substantially. Other sodium nonatitanate powders of varying crystallinities also showed rapid kinetics. Other potentially suitable binders for forming suitable pellets include titanium isopropoxide or tetraethyl orthosilicate (TEOS) as a binder precursor.

Example 10

82Sr Removal from Irradiated Targets Using Pelletized Sodium Nonatitanate

A sample of sodium nonatitanate was mixed with titanium isopropoxide as a binder and the resulting paste dried at 105° C. for 12 hours. The material was gently broken up using a mortar and pestle and then sieved to produce particles in the range 40 to 60 mesh. The binder content was approximately 20%. These particles were then used to assess the extraction of 89Sr from simulated target solutions.

1 mL of pelletized sodium nonatitanate was slurried into a column and the target simulant that had been spiked with 89Sr to give an activity of approximately 200,000 cpm/mL was passed through the column at a flow rate of 15 mL per hour. The amount of activity removed from solution was then determined. The results are given below in Table 1.

TABLE 1

Removal of 82Sr From Irradiated Target Solutions

| Target | Solution Composition | Volume (mL) | 82Sr Removed (%) |
|---|---|---|---|
| Rubidium Metal | 1.95M RbCl in 0.1M $NH_3$/$NH_4Cl$ Buffer, pH 10 | 20 | 97.3 |
| Rubidium Chloride | 0.68M RbCl in 0.1M $NH_3$/$NH_4Cl$ Buffer, pH 10 | 20 | 98.8 |
| Molybdenum Metal | 0.26M $Na_2MoO_4$, pH 12 | 20 | 99.9 |

This data clearly shows the effectiveness of sodium nonatitanate at removing strontium isotopes from 82Sr target materials. Rubidium absorption under these conditions is minimal.

Example 11

Elution of Strontium

Strontium was quantitatively eluted from the sodium nonatitanate column of Example 10 using 6M nitric acid. Hydrochloric acid was found to be much less effective and also resulted in breakdown of the sodium nonatitanate particles and blocked the ion exchange column.

While the foregoing is directed to the preferred embodiment of the present invention, other and further embodiments of the invention may be devised without departing from the basic scope thereof, and the scope thereof is determined by the claims that follow.

What is claimed is:

1. A process for preparing a rubidium-82 generator, comprising:
   (a) preparing sodium nonatitanate from titanium isopropoxide and aqueous sodium hydroxide;
   (b) heating the sodium nonatitanate at a temperature between 100° C. and 250° C. for a period between 12 hours and 2 weeks; and
   (c) absorbing strontium-82 on the sodium nonatitanate from an aqueous solution comprising strontium-82 and sodium chloride, wherein the sodium chloride concentration is between 0.1 and 1 molar.

2. The process of claim 1, wherein the molar ratio of aqueous sodium hydroxide to titanium isopropoxide is in excess of 0.44.

3. The process of claim 1, wherein the molar ratio of aqueous sodium hydroxide to titanium isopropoxide is between 2 and 6.

4. The process of claim 1, wherein the aqueous sodium hydroxide is about 50 wt % sodium hydroxide.

5. The process of claim 1, further comprising:
   filtering the sodium nonatitanate from the solution.

6. The process of claim 5, further comprising:
washing the sodium nonatitanate with ethanol.

7. The process of claim 6, further comprising:
drying the sodium nonatitanate.

8. The process of claim 1, wherein the molar ratio of aqueous sodium hydroxide to titanium isopropoxide is between 1 and 10.

9. The process of claim 1, wherein the sodium nonatitanate is heated in a pressure vessel.

10. The process of claim 1, wherein the sodium nonatitanate is prepared in the absence of titanium chlorides and sulfates.

11. A method of chemically isolating strontium-82 from a proton-irradiated molybdenum target, comprising:
(a) dissolving the molybdenum metal target containing the strontium-82;
(b) adjusting the pH of the dissolved molybdenum target solution to an alkaline pH;
(c) removing precipitates from the solution; and then
(d) absorbing the strontium-82 from the solution onto a support comprising sodium nonatitanate.

12. The method of claim 11, wherein the molybdenum target is dissolved in hydrogen peroxide.

13. The method of claim 11, wherein the pH is adjusted with sodium hydroxide.

14. The method of claim 11, wherein the pH is adjusted to about 12.

15. The method of claim 11, further comprising:
stripping the strontium-82 from the sodium nonatitanate.

16. The method of claim 15, wherein the strontium-82 is stripped from the sodium nonatitanate with mineral acid.

17. The method of claim 11, further comprising:
washing the sodium nonatitanate with a buffer solution.

18. The method of claim 11, wherein the sodium nonatitanate is characterized by a strontium/rubidium separation factor greater than 12,500.

19. The method of claim 11, wherein the sodium nonatitanate is characterized by a strontium/rubidium separation factor greater than or equal to 59,200.

20. The method of claim 11, wherein the sodium nonatitanate is characterized by a strontium/rubidium separation factor greater than or equal to 100,000.

21. A process for preparing a solution containing rubidium-82, comprising:
(a) providing a solution containing strontium-82;
(b) absorbing strontium-82 onto a sodium nonatitanate support medium; and
(c) eluting rubidium-82 from the sodium nonatitanate support medium with a solvent.

22. The process of claim 21, wherein the solvent is selected from the group consisting of water and saline solutions.

23. The process of claim 21, wherein the solvent is an aqueous solution having a sodium chloride concentration between 0.001 molar and 1 molar.

24. The process of claim 21, wherein the solvent is an aqueous solution having a sodium chloride concentration between 0.2 molar and 1 molar.

25. The process of claim 21, wherein the solvent is a pharmaceutical-grade saline and buffer solution.

26. The process of claim 21, wherein the sodium nonatitanate is characterized a strontium/rubidium separation factor greater than 12,500.

27. The process of claim 21, wherein the sodium nonatitanate is characterized a strontium/rubidium separation factor greater than or equal to 59,200.

28. The process of claim 21, wherein the sodium nonatitanate is characterized a strontium/rubidium separation factor greater than or equal to 100,000.

29. The process of claim 21, further comprising:
disposing the sodium nonatitanate support medium into a column.

30. The process of claim 21, wherein the solvent containing the eluted rubidium is alkaline.

31. The process of claim 21, further comprising:
buffering the solvent.

32. The process of claim 21, wherein the solution containing strontium-82 is an acidic aqueous solution.

33. The process of claim 21, wherein the solution containing strontium-82 is an alkaline aqueous solution.

34. A method of chemically isolating strontium-82 from a proton-irradiated rubidium or rubidium chloride target, comprising:
(a) dissolving the target containing the strontium-82;
(b) adjusting the pH of the dissolved target solution to an alkaline pH;
(c) removing precipitates from the solution; and then
(d) absorbing the strontium-82 from the solution onto a support comprising sodium nonatitanate without absorbing rubidium.

35. The method of claim 34, wherein the dissolved target solution includes a buffer.

36. The method of claim 35, wherein the buffer is an ammonia/ammonium chloride buffer.

37. The method of claim 35, wherein the pH is between 9 and 10.

38. The method of claim 34, wherein the pH is greater than 10.

39. The method of claim 34, further comprising:
stripping the strontium-82 from the sodium nonatitanate.

40. The method of claim 39, wherein the strontium-82 is stripped from the sodium nonatitanate with mineral acid.

41. The method of claim 34, further comprising:
washing the sodium nonatitanate with a buffer solution.

42. The method of claim 34, wherein the sodium nonatitanate is characterized by a strontium/rubidium separation factor greater than 12,500.

43. The method of claim 34, wherein the sodium nonatitanate is characterized by a strontium/rubidium separation factor greater than or equal to 59,200.

44. The method of claim 34, wherein the sodium nonatitanate is characterized by a strontium/rubidium separation factor greater than or equal to 100,000.

45. A rubidium-82 generator, comprising:
a strontium-82 support medium comprising sodium nonatitanate characterized by a strontium/rubidium separation factor greater than 12,500 at an alkaline pH; and
strontium-82 absorbed on the sodium nonatitanate.

46. The rubidium-82 generator of claim 45, wherein the separation factor is determined in an aqueous sodium chloride solution.

47. The rubidium-82 generator of claim 46, wherein the aqueous sodium chloride solution has a sodium chloride concentration from 0.001 molar to 1 molar.

48. The rubidium-82 generator of claim 46, wherein the aqueous sodium chloride solution is buffered to control acidity.

49. The rubidium-82 generator of claim 46, wherein the aqueous sodium chloride solution is unbuffered.

50. The rubidium-82 generator of claim 45, wherein the sodium nonatitanate is characterized by a strontium selectivity greater than about 85,000 mL/g in a 0.1 molar or 1 molar aqueous sodium chloride solution.

51. The rubidium-82 generator of claim 50, wherein the aqueous sodium chloride solution is unbuffered.

52. The rubidium-82 generator of claim 45, wherein the sodium nonatitanate is characterized by a rubidium selectivity less than 100 mL/g in a 0.1 molar aqueous sodium chloride solution.

53. The rubidium-82 generator of claim 52, wherein the aqueous sodium chloride solution is unbuffered.

54. The rubidium-82 generator of claim 45, wherein the sodium nonatitanate is characterized by a strontium/rubidium separation factor greater than 10,000 in a 1 molar aqueous sodium chloride solution.

55. The rubidium-82 generator of claim 45, wherein the sodium nonatitanate is characterized by a rubidium retention of less than 1.8% in a 1 molar aqueous sodium chloride solution.

56. The rubidium-82 generator of claim 45, wherein the sodium nonatitanate is characterized by a rubidium retention of less than about 13.6% in a 0.1 molar aqueous sodium chloride solution.

57. The rubidium-82 generator of claim 45, wherein the sodium nonatitanate is characterized by a rubidium retention of less than about 40% in a 0.01 molar aqueous sodium chloride solution.

58. The rubidium-82 generator of claim 45, wherein the sodium nonatitanate is characterized by a rubidium retention of less than about 50% in a 0.001 molar aqueous sodium chloride solution.

59. The rubidium-82 generator of claim 45, wherein the generator contains less than 1 gram of sodium nonatitanate.

60. A rubidium-82 generator, comprising:
a strontium-82 support medium comprising sodium nonatitanate characterized by a strontium/rubidium separation factor greater than 12,500 at an alkaline pH; and
a sodium nonatitanate filter medium disposed to receive effluent from the strontium-82 support medium to trap strontium-82 leached from the generator.

61. A rubidium-82 generator, comprising:
a strontium-82 support medium comprising sodium nonatitanate characterized by a strontium/rubidium separation factor greater than 12,500 at an alkaline pH; and
a column, wherein the sodium nonatitanate is disposed in the column.

62. A rubidium-82 generator, comprising:
a strontium-82 support medium comprising sodium nonatitanate is characterized by a strontium/rubidium separation factor greater than 59,200 at an alkaline pH.

63. The rubidium-82 generator of claim 62, wherein the sodium nonatitanate is characterized by a strontium/rubidium separation factor greater than or equal to 79,500.

64. The rubidium-82 generator of claim 62, wherein the sodium nonatitanate is characterized by a strontium selectivity greater than 250,000 mL/g at an alkaline pH.

65. The rubidium-82 generator of claim 62, wherein the sodium nonatitanate is characterized by a rubidium selectivity less than 100 mL/g at an alkaline pH.

66. The rubidium-82 generator of claim 63, wherein the sodium nonatitanate is characterized by a strontium/rubidium separation factor greater than 100,000.

67. The rubidium-82 generator of claim 62, wherein the sodium nonatitanate has not undergone hydrothermal treatment.

68. The rubidium-82 generator of claim 66, wherein the sodium nonatitanate has not undergone hydrothermal treatment.

69. A process for preparing a rubidium-82 generator, comprising:
preparing sodium nonatitanate from titanium tetrachloride or titanium sulfate and aqueous sodium hydroxide;
heating the sodium nonatitanate at a temperature between 100° C. and 250° C. for a period between 12 hours and 2 weeks; and
absorbing strontium-82 on the sodium nonatitanate from an aqueous solution comprising strontium-82 and a soluble sodium salt, wherein the soluble sodium salt concentration is between 0.1 and 1 molar.

70. The process of claim 69, wherein the soluble sodium salt is sodium chloride.

71. The process of claim 69, wherein the aqueous sodium hydroxide is about 50 wt % sodium hydroxide.

72. The process of claim 69, wherein the molar ratio of aqueous sodium hydroxide to titanium tetrachloride or titanium sulfate is between about 1 and 12.

73. The process of claim 69, wherein the sodium nonatitanate is filtered from the mixture.

74. The process of claim 73, wherein the sodium nonatitanate is washed to remove sodium chloride or sodium sulfate.

75. A process for preparing a rubidium-82 generator, comprising:
(a) preparing sodium nonatitanate from titanium isopropoxide and aqueous sodium hydroxide;
(b) heating the sodium nonatitanate at a temperature between 100° C. and 250° C. for a period between about 12 hours and about 2 weeks; and
(c) absorbing strontium-82 on the sodium nonatitanate from an aqueous solution comprising strontium-82 and a soluble sodium salt.

76. The process of claim 75, wherein the molar ratio of aqueous sodium hydroxide to titanium isopropoxide is in excess of 0.44.

77. The process of claim 75, wherein the molar ratio of aqueous sodium hydroxide to titanium isopropoxide is between 2 and 6.

78. The process of claim 75, wherein the aqueous sodium hydroxide is about 50 wt % sodium hydroxide.

79. The process of claim 75, wherein the soluble sodium salt concentration is between 0.1 and 1 molar.

80. The process of claim 75, further comprising:
loading the sodium nonatitanate into a column alter absorbing strontium-82.

81. The process of claim 80, characterized by uniform loading of strontium-82 throughout the sodium nonatitanate.

82. A process, comprising:
eluting a solution of rubidium-82 from a strontium-82 support medium comprising sodium nonatitanate with an aqueous solvent.

83. The process of claim 82, wherein the aqueous solvent is selected from the group consisting of water and saline solutions.

84. The process of claim 82, wherein the aqueous solvent has a sodium chloride concentration between 0.001 molar and 1 molar.

85. The process of claim 82, wherein the aqueous solvent has a sodium chloride concentration between 0.2 molar and 1 molar.

86. The process of claim 82, wherein the aqueous solvent is a saline and buffer solution suitable for human injection.

87. The process of claim 82, wherein the sodium nonatitanate is a reaction product of titanium isopropoxide and aqueous sodium hydroxide.

88. The process of claim 82, further comprising passing the rubidium-82 solution through a sodium nonatitanate filter to selectively remove any strontium-82 or strontium-85 from the solution.

89. The process of claim 82, further comprising disposing of the sodium nonatitanate filter.

90. The process of claim 82, further comprising using the rubidium-82 solution as a medical diagnostic agent or medical imaging agent.

91. The process of claim 82, further comprising injecting the rubidium-82 solution intravenously.

92. The process of claim 82, further comprising stripping strontium-82 from the sodium nonatitanate.

93. The process of claim 92, further comprising recovering the stripped strontium-82.

94. The process of claim 92, further comprising recycling the sodium nonatitanate.

95. The process of claim 82, wherein the sodium nonatitanate has not undergone hydrothermal treatment.

* * * * *

UNITED STATES PATENT AND TRADEMARK OFFICE
CERTIFICATE OF CORRECTION

PATENT NO. : 6,908,598 B2
DATED : June 21, 2005
INVENTOR(S) : Paul Sylvester

It is certified that error appears in the above-identified patent and that said Letters Patent is hereby corrected as shown below:

Title page,
Item [54], Title, replace "RUBIDLUM" with -- RUBIDIUM --.

Signed and Sealed this

Twenty-third Day of August, 2005

JON W. DUDAS
*Director of the United States Patent and Trademark Office*